(12) United States Patent
Johs et al.

(10) Patent No.: US 6,483,586 B1
(45) Date of Patent: Nov. 19, 2002

(54) BEAM SPLITTING ANALYZER MEANS IN ROTATING COMPENSATOR ELLIPSOMETER

(75) Inventors: Blaine D. Johs, Lincoln, NE (US); Craig M. Herzinger, Lincoln, NE (US); Steven E. Green, Lincoln, NE (US); Jeffrey S. Hale, Lincoln, NE (US)

(73) Assignee: J. A. Woollam Co. Inc., Lincoln, NE (US)

( * ) Notice: Subject to any disclaimer, the term of this patent is extended or adjusted under 35 U.S.C. 154(b) by 0 days.

(21) Appl. No.: 09/950,036

(22) Filed: Sep. 10, 2001

Related U.S. Application Data

(63) Continuation-in-part of application No. 09/496,011, filed on Feb. 1, 2000, now Pat. No. 6,353,477, which is a continuation-in-part of application No. 08/912,211, filed on Aug. 15, 1997, now Pat. No. 5,872,630, which is a continuation-in-part of application No. 08/530,892, filed on Sep. 20, 1995, now Pat. No. 5,666,201.

(60) Provisional application No. 60/231,989, filed on Sep. 11, 2000.

(51) Int. Cl.$^7$ ............................................. G01N 21/21
(52) U.S. Cl. ................................................... 356/369
(58) Field of Search ................................ 356/369, 364, 356/365, 366, 367, 368; 250/225

(56) References Cited

U.S. PATENT DOCUMENTS

| 5,002,371 A | 3/1991 | Wright ........................ 350/394 |
|---|---|---|
| 5,416,588 A | 5/1995 | Ducharme et al. .......... 356/369 |
| 5,581,350 A | 12/1996 | Chen et al. .................. 356/369 |
| 5,706,212 A | 1/1998 | Thompson et al. ......... 356/369 |
| 5,872,630 A | 2/1999 | Johs et al. .................... 356/369 |
| 5,946,098 A | 8/1999 | Johs et al. .................... 356/364 |
| 5,963,325 A | 10/1999 | Johs et al. .................... 356/364 |
| 6,084,675 A | 7/2000 | Herzinger et al. .......... 356/364 |
| 6,100,981 A | 8/2000 | Johs et al. .................... 356/364 |
| 6,118,537 A | 9/2000 | Johs et al. .................... 356/369 |
| 6,141,102 A | 10/2000 | Johs et al. .................... 356/364 |
| 6,084,674 A1 | 7/2002 | Johs et al. .................... 356/364 |

FOREIGN PATENT DOCUMENTS

SU           1432439       10/1988

OTHER PUBLICATIONS

Four Pages of Beam Splitting Elements, Product Literature.
Regression Calibration Method for Rotating Element Ellipsometers, Johs, Thin Solid Films, 234 (1993). Said paper is disclosed as it describes a mathematical regression based approach to calibrating ellipsometer systems.
"A Two–Channel Polarization Modulation Ellipsometer", Jellison & Modine, Appl. Opt., (Oct. 1990).
"Automatic Rotating Element Ellipsometers: Calibrations, Operation and Real–Time Applications", Collins, Rev. Sci. Instrum., 61(8) (1990)

Primary Examiner—Hoa Q. Pham
(74) Attorney, Agent, or Firm—James D. Welch

(57) ABSTRACT

Disclosed is a rotating compensator sample system investigation system which includes a source of a beam of electromagnetic radiation, a polarizer, a stage for supporting a sample system, a beam splitting analyzer, and at least two detector systems which are positioned each to intercept a different of the at least two electromagnetic beams which emerge from the beam splitting analyzer. Also disclosed is a regression based approach to calibration which simultaneously extracts a sample system PSI and DELTA.

17 Claims, 7 Drawing Sheets

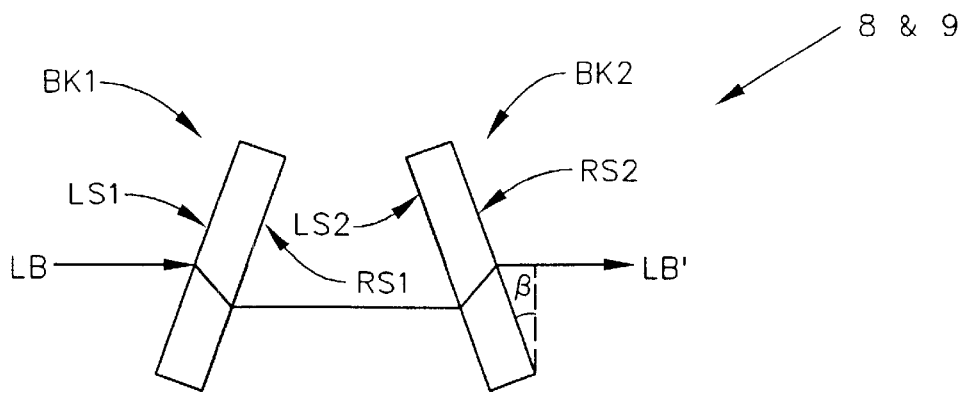
FIG. 8j₁
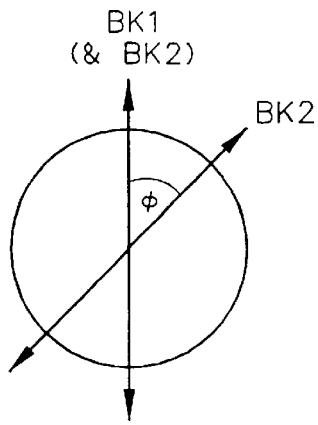
FIG. 8j₂
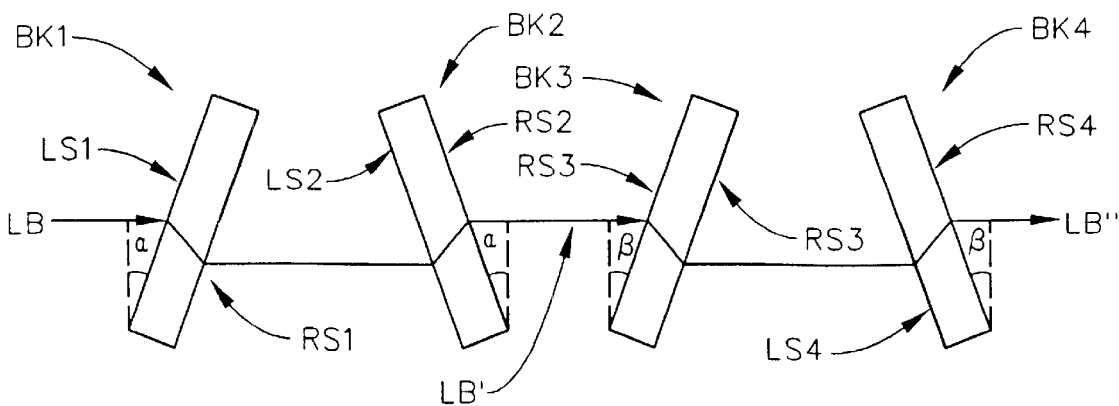
FIG. 8k₁

BEAM SPLITTING ANALYZER MEANS IN ROTATING COMPENSATOR ELLIPSOMETER

This Application is a CIP from application Ser. No. 09/496,011 filed Feb. 1, 2000 now U.S. Pat. No. 6,353,477, which Application was a CIP from application Ser. No. 08/912,211, filed Aug. 15, 1997, (now U.S. Pat. No 5,872, 630), which was a CIP from application Ser. No. 08/530, 892, filed Sep. 20, 1995, (now U.S. Pat. No. 5,666,201). This Application is further a CIP from Provisional Patent Application Ser. No. 60/231,989 filed Sep. 11, 2000.

TECHNICAL FIELD

The present invention relates to Rotating Compensator Sample System Investigation Systems and more particularly to use of Beam Splitting Analyzer means therein to simultaneously provide two electromagnetic beams, each thereof having a different effective Analyzer Azimuthal angle imposed thereupon. In use each of said two beams of electromagnetic radiation is directed to a separate detector such that two corresponding data sets are simultaneously, rather than sequentially as required where conventional Rotatable Analyzer means are utilized, obtained.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

Continuing, in general, modern practice of ellipsometry typically involves causing a spectroscopic beam of electromagnetic radiation, in a known state of polarization, to interact with a sample system at at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system:

$$PSI = |r_p/r_s|;$$

and $$DELTA = (\Delta r_p - \Delta r_s).$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Spectroscopic Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. It is noted that nulling ellipsometers, in which elements therein are rotatable rather than rotating, and that ellipsometers containing modulation elements also are known.

Continuing, in use, data sets can be obtained with an ellipsometer system configured:

with a sample system present,
sequentially for cases where other sample systems are present, and
where the ellipsometer system is configured in a straight-through configuration wherein a beam of electromagnetic radiation is caused to pass straight through the ellipsometer system without interacting with a sample system.

Simultaneous mathematical regression utilizing multiple data sets can allow calibration of ellipsometers and evaluation of sample system characterizing PSI and DELTA values. The obtaining of numerous data sets with an ellipsometer system configured with, for instance, a sequence of sample systems present and/or wherein a sequential plurality of polarization and/or analyzer azimuthal angle states are imposed on an electromagnetic beam caused to interact with one or more sample systems, can allow system calibration of numerous ellipsometer system variables. It is noted, however, that it is often inconvenient to have to sequentially reconfigure an ellipsometer system to obtain multiple data sets. It is that problem to which the present invention provides an answer.

As it is relevant to the present invention it is noted at this point that polarizer and analyzer elements often comprise rotatable elements which serve to provide, or detect, a single beam of linearly polarized electromagnetic radiation, and that multiple data sets can correspond to multiple azimuthal angle rotation positions of said analyzer.

With the present invention in mind it is disclosed that relevant Patents include U.S. Pat. No. 5,872,630 to Johs et al., (said 630 Patent being incorporated by reference hereinto), which describes a Rotating Compensator Ellipsometer System. Said 630 Patent rotating compensator ellipsometer is described as being a sample system investigation system comprising a source of a beam of electromagnetic radiation, a polarizer, a stage for supporting a sample system, an analyzer, and a detector system, said rotating compensator sample system investigation system further comprises at least one compensator(s) positioned at a location selected from the group consisting of:

before said stage for supporting a sample system; and
after said stage for supporting a sample system; and
both before and after said stage for supporting a sample system;

such that when said rotating compensator sample system investigation system is used to investigate a sample system present on said stage for supporting a sample system, said polarizer means and analyzer means are maintained essentially fixed in position and at least one of said at least one compensator(s) is caused to continuously rotate while a beam of electromagnetic radiation produced by said source of a beam of electromagnetic radiation is caused to pass through said polarizer means and said at least one compensator(s), said beam of electromagnetic radiation being also caused to interact with said sample system and pass through said analyzer means and enter said detector system.

Further disclosed is a U.S. Pat. No. 5,416,588 to Ducharme which describes use of a Wollaston Prism as an Analyzer beam splitting means in said Modulation Element Ellipsometer System.

U.S. Pat. No. 5,946,098 to Johs et al. is disclosed as providing numerous designs for compensators which can be used in a present invention system. Said 098 Patent is incorporated by reference herewithin.

As the present invention includes regression calibration, a Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein. Said 212 Patent is incorporated by reference herewithin.

Also, while not citing the Johs paper, a Patent to Chen et al., U.S. Pat. No. 5,581,350, describes regression calibration of ellipsometer systems.

Patents which describe compensator systems for application in present invention systems are:

U.S. Pat. No. 5,963,325;
U.S. Pat. No. 5,946,098;
U.S. Pat. No. 6,084,674;
U.S. Pat. No. 6,084,675;
U.S. Pat. No. 6,100,981;
U.S. Pat. No. 6,118,537; and
U.S. Pat. No. 6,141,102.

U.S. Pat. No. 5,002,371 to Wright and Russian Patent No. SU 1432439 are also mentioned as they describe means for beam splitting.

A paper, which is incorporated by reference herewithin, is by Johs, and titled "Regression Calibration Method for Rotating Element Ellipsometers", Thin Solid Films, 234 (1993). Said paper is disclosed as it describes a mathematical regression based approach to calibrating ellipsometer systems.

Further cited is a paper titled "A Two-Channel Polarization Modulation Ellipsometer", Jellison & Modine, Appl. Opt., (October 1990).

Even in view of relevant prior art, there remains need for a more convenient approach to simultaneously providing multiple data sets in the context of rotating compensator material system investigation systems. The present invention responds to said identified needs.

DISCLOSURE OF THE INVENTION

The 630 Patent to Johs et al. cited in the Background Section of this Specification describes, in the context of a Rotating Compensator Sample System Investigation System, describes the presence of Rotatable Polarizer and Analyzer elements which can be set to various static positions during data acquisition, during which data acquisition at least one present Compensator is caused to rotate. To calibrate said system it is typically required that two data sets be obtained, which data sets can correspond to two azimuthal angle settings of the Analyzer and/or Polarizer element.

The present invention rotating compensator sample system investigation system comprises a source of a beam of electromagnetic radiation, a polarizer, a stage for supporting a sample system, a beam splitting analyzer means, and at least two detector systems, each said detector system being positioned to separately intercept one of at least two beams which emerge from said beam splitting analyzer means; said rotating compensator sample system investigation system further comprising at least one compensator(s) positioned at a location selected from the group consisting of:

before said stage for supporting a sample system; and
after said stage for supporting a sample system; and
both before and after said stage for supporting a sample system.

It is specifically noted that the present invention rotating compensator sample system Investigation system differs from that disclosed in the 630 Patent, (and from all other known similar Rotating Compensator based systems), in that in place of a Rotatable Analyzer and a Single Detector, (typically comprising multiple detector elements), there is present:

a beam splitting analyzer means, and at least two detector systems, each said detector system being positioned to separately intercept one of at least two beams of electromagnetic radiation which emerge from said beam splitting analyzer means . . .

In use, when said present invention rotating compensator sample system investigation system is used to investigate a sample system present on said stage for supporting a sample system, said polarizer means and beam splitting analyzer means are maintained essentially fixed in position and at least one of said at least one compensator(s) is caused to continuously rotate while a beam of electromagnetic radiation produced by said source of a beam of electromagnetic radiation is caused to pass through said polarizer means and said at least one compensator(s), said beam of electromagnetic radiation being also caused to interact with said sample system and pass through said beam splitting analyzer means such that two beams of electromagnetic radiation, (eg. affected to correspond to two azimuthal positions of a conventional analyzer means), are simultaneously caused to each separately enter different of said at least two detector systems.

A method of calibrating a rotating compensator sample system investigation system while extracting sample system PSI and DELTA values, comprising the steps of:

a. providing a rotating compensator sample system investigation system as described above; in either order practicing steps b. and steps (c. and d.):

b. developing a mathematical model of said rotating compensator sample system investigation system which comprises as calibration parameter variables polarizer azimuthal angle orientation, present sample system PSI, present sample system DELTA, compensator azimuthal angle orientation(s), matrix components of said at least one compensator(s), and effective beam splitting analyzer means azimuthal angle orientations, which mathematical model is effectively a transfer function which enables calculation of electromagnetic beam intensity as a function of wavelength detected by a detector when given intensity as a function of wavelength provided by said source of a beam of electromagnetic radiation;

c. causing a beam of electromagnetic radiation produced by said source of a beam of electromagnetic radiation, to pass through said polarizer, interact with a sample system caused to be in the path thereof, pass through said beam splitting analyzer means such that at least two beams emerge therefrom with each thereof entering a different one of said at least two detector systems; said beam of electromagnetic radiation also being caused to pass through said compensator(s) positioned at a location selected from the group consisting of:

before said stage for supporting a sample system;

after said stage for supporting a sample system; and both before and after said stage for supporting a sample system;

d. simultaneously obtaining two data sets of intensity values, corresponding to the effective azimuthal angles of two beams of electromagnetic radiation exiting said beam splitting analyzer means over time, while at least one of said at least one compensator(s) is caused to continuously rotate;

e. performing a mathematical regression of said mathematical model onto said at least two data sets;

said regression based calibration procedure serving to compensate said mathematical model for azimuthal angles of said polarizer, said at least one compensator(s), matrix elements of said at least one compensator(s), and said two effective analyzer angles, in addition evaluating the PSI and DELTA of the present sample system.

Said method of calibrating a rotating compensator sample system investigation system can further comprise, in the step d. simultaneously obtaining two data sets of intensity values vs. effective azimuthal angles of said beam splitting analyzer means for each of two sample systems; and in step e. including simultaneous regression onto data for both sample systems.

Finally, as the present invention comprises a rotating compensator, it is noted that any functional compensator can be utilized, however, for reference, a catalog of suitable Compensators, (many Patented by the J. A. Woollam Co.), are recited directly. Compensators disclosed in co-pending patent application Ser. No. 09/496,011 are:

a single element compensator;

a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB)).

Additional compensator systems, previously disclosed in patent application Ser. No. 08/997,311, (now U.S. Pat. No. 5,946,098 which is incorporated herewithin), and CIP's therefrom, which compensators are specifically within the scope of application with the present invention are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

The present invention will be better understood by reference to the Detailed Description Section of this Specification, in conjunction with the Drawings.

SUMMARY OF THE INVENTION

It is therefore a primary objective and/or purpose of the present invention to teach a rotating compensator sample system investigation system which comprises a source of a beam of electromagnetic radiation, a polarizer, a stage for supporting a sample system, a beam splitting analyzer means, and two detector systems, each said detector system being positioned to separately intercept one of at least two beams which emerges from said beam splitting analyzer means; said rotating compensator sample system investigation system further comprising at least one compensator(s).

It is another objective and/or purpose of the present invention to teach regression based calibration and extraction of sample system PSI and DELTA values.

Other objectives and/or purposes of the present invention will become apparent by a reading of the Specification and Claims.

BRIEF DESCRIPTION OF THE DRAWINGS

FIGS. 8a–8i demonstrate functional construction of preferred present invention compensator systems.

FIGS. 8j1–8l show additional functional construction of compensator systems which are within the scope of the present invention.

DETAILED DESCRIPTION

Figure 1:
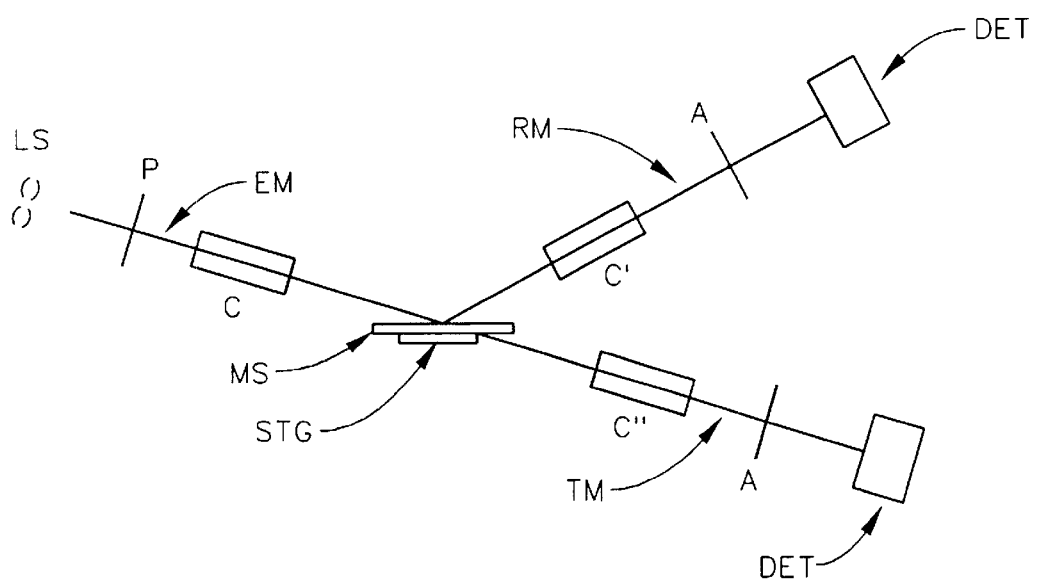
FIG. 1 demonstrates a typical Rotating Compensator Sample System Investigation System.

Turning now to FIG. 1 it is shown that a typical Rotating Compensator Sample System Investigation System, specifically exemplified by a Rotating Compensator Ellipsometer System, is comprised of:

Source of Electromagnetic Radiation (LS);
Polarizer means (P);
Means (STG) for supporting a Sample System;
Analyzer means (A);
Detector means (DET);
with at least one Compensator selected from (C) (C') (C"),
which Compensator is caused to rotate about the locus of a beam of Electromagnetic radiation passing therethrough, which Electromagnetic radiation interacts with a Sample System (MS) placed on the Means (STG) for supporting a Sample System, being present between the Polarizer means (P) and Analyzer means (A). FIG. 1 shows both Reflection (RM) and Transmission (TM) Electromagnetic Radiation Modes, (as does FIG. 2).

In use electromagnetic radiation proceeding to the Analyzer means (A) after interaction with a Sample System (SS) and a Compensator (C) (C') (C") which is caused to rotate, is typically passed through said Analyzer means (A) to a Detector (DET) with the Analyzer means (A) set first to Azimuthal +45, and then Azimuthal −45 Degrees. (Note, the Analyzer means (A) in FIG. 1 is typically a single beam providing means situated in a rotatable element). This provides sufficient data to cancel Azimuthal error, and to calibrate all mathematical parameter representations of components, along with evaluating Sample System PSI and DELTA. This however, requires means to set the Analyzer means (A) in two, (eg. +/−45 degrees), positions while obtaining two corresponding data sets.

It should be apparent that it would be of benefit if the two sets of data, effectively corresponding to two Analyzer means (A) Azimuthal angles, could be obtained without the requirement to rotate an Analyzer means (A) to two different positions. (Note, a conventional Analyzer (A) is typically functionally an element which can be rotated into selected Azimuthal angles).

Figure 2:
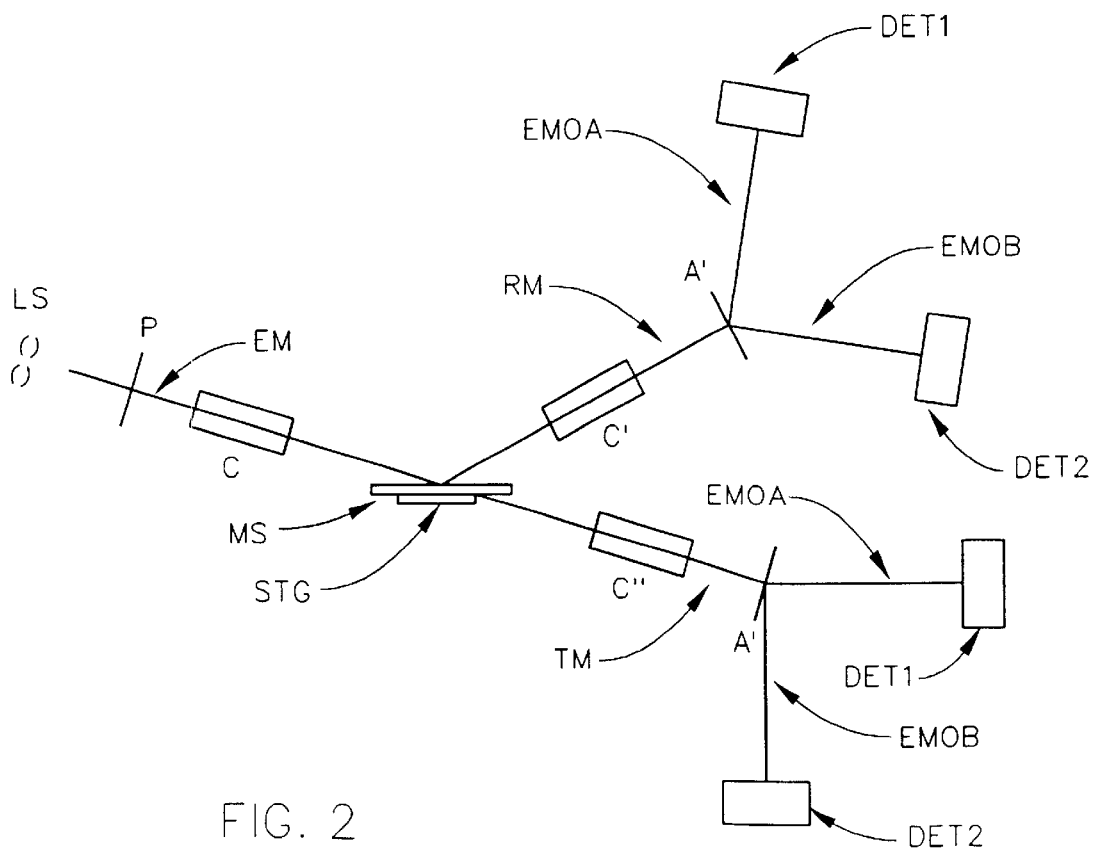
FIG. 2 shows the Rotating Compensator Ellipsometer System of FIG. 1, but modified in accordance with the present invention to include a Beam Splitting Analyzer means (A) which produces a demonstrative two beam of electromagnetic radiation.

The present invention, as demonstrated in FIG. 2, provides a Beam Splitting Analyzer means (A') in place of the Analyzer (A) in FIG. 1, which Beam Splitting Analyzer means (A') accepts entry of a single beam of electromagnetic radiation and emits two beams of electromagnetic radiation which have, respectively, first, and second effective Azimuthal Analyzer angles, with said first second effective Azimuthal angles typically being complimentary, to the another. Where the Beam Splitting Analyzer demonstrates said complimentary results, if the Beam Splitting Analyzer means (A') is oriented to provide the first exiting Electromagnetic beam at an effective Analyzer Azimuthal Angle of +/−45 degrees, the second electromagnetic beam will be have an effective Analyzer Azimuthal Angle of −/+45 degrees, although in practice it has not been found necessary to be particularly accurate in the +/−45 degree settings. For instance, angle pairings such as +/−20 and −/+70 degrees provide sufficient data sets, as do many other angle pairings. (Note, an "Effective Analyzer Azimuthal Angle" imposed by a Beam Splitting Analyzer means (A') is one that affects electromagnetic radiation passing therethrough as does a conventional Analyzer which is rotated to that "Azimuthal angle").

FIG. 2 identifies that a drawback of using the Beam Splitting Analyzer means (A') is that Two Detectors (DET1) (DET2) are required to be positioned such that one intercepts the first, and the other the second of the electromagnetic beams exiting the Beam Splitting Analyzer means (A'). (Note, the physical positioning of the Detectors (DET1) and (DET2) in FIG. 2 is determined by how to intercept the two electromagnetic beams exiting the Beam Splitting Analyzer means (A) and, and is not indicative of Analyzer affect, (eg. +/−45 Degrees), inherent in the exiting electromagnetic beams).

Further, while one said Electromagnetic beam exiting off-the-shelf available Beam Splitting Analyzer means (A') is found to be essentially achromatically affected by the Beam Splitting Analyzer means (A'), the other is not. This imposes a limitation which, while not a problem where only one wavelength, (ie. monochromatic electromagnetic radiation), is utilized, can cause calibration difficulties where spectroscopic electromagnetic radiation is utilized and spectroscopic data sets are acquired. Thus, presently preferred application of the present invention is with monochromatic electromagnetic radiation, although a spectroscopic system is within the scope of the present invention, particularly where regression calibration is applied to compensate achromatic effects. (Note, a benefit of regression based calibration is that non-idealities of system components can be relatively easily accounted for. It is this fact which allows the J. A. Woollam CO. M-2000, (see 630 Patent to Johs), to achieve superior results when operated with off-the-shelf compensators, where other approaches to calibration require essentially achromatic compensators be utilized).

Exemplary materials from which Beam Splitting Analyzer means (A') can be made are MgF, and Calcite, and types thereof can be:

Beam Splitting Thompson;
Two and Three Element Wollaston Prism Polarizers;
Glan-Laser Single and Double Escape Window(s); and
Rochon Beam Splitting Prism Polarizers, etc.

Figure 3:
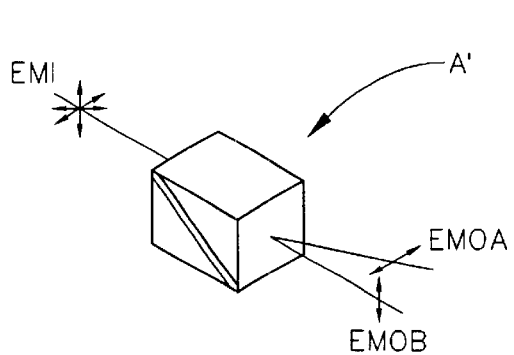
FIG. 3 demonstrates Rochon or Wollaston Prism Polarizer.
Figure 4:
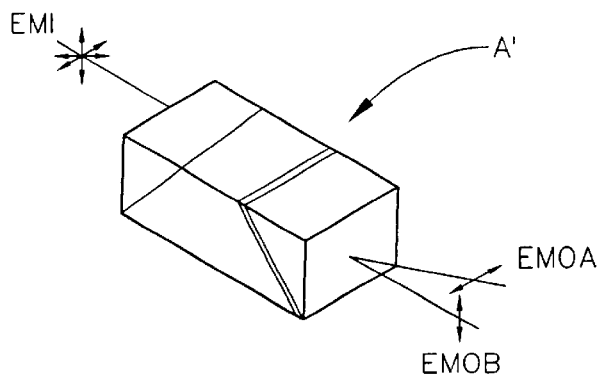
FIG. 4 demonstrates a three-element Wollaston Prism Polarizer.
Figure 5:
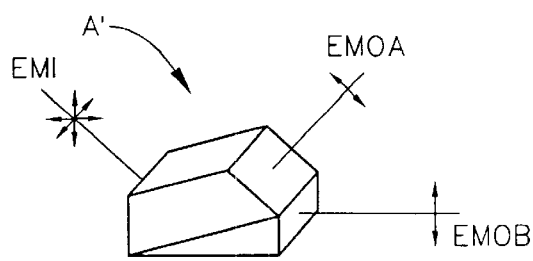
FIG. 5 demonstrates a Beam Splitting Thompson Prism Polarizer.
Figure 6:
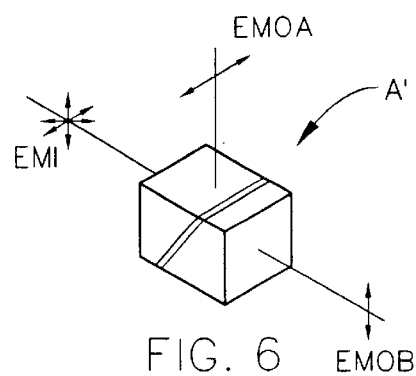
FIGS. 6 and 7 demonstrate Glan-Laser Single and Double Escape Windows.
Figure 7:
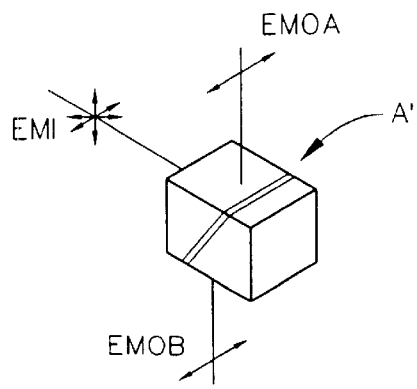

For insight to the construction of the FIG. 2 Beam Splitting Analyzer means (A'), FIG. 3 shows demonstrates a Rochon and Wollaston Prism Polarizer structures, FIG. 4 demonstrates a three-element Wollaston Prism Polarizer, FIG. 5 demonstrates a Beam Splitting Thompson Prism Polarizer and FIGS. 6 and 7 demonstrate Glan-Laser Single and Double Escape Windows. In each of the FIGS. 3–7 it should be noted that a single beam in (EMI), two physically separate beams out (EMOA) and (EMOB) are present.

It is noted that while to do such is within the scope of the present invention, there is typically no need to calibrate the present rotating compensator invention system in a regression procedure separate from that which simultaneously evaluates PSI and DELTA of a sample system. This is because for each data set, D.C., and 2ω and 4ω ALPHA and BETA coefficients are obtained, and only Azimuthal angles for the Polarizer, Compensator, an Effective Analyzer Azimuthal Angle and Sample System PSI and DELTA need be evaluated. Hence sufficient data is available to directly evaluate all required parameters. However, should non-idealities in any element require calibration, (eg. compensator achromaticity), the present invention teaches sequentially obtaining at least two data sets for each of a plurality of sample systems, and doing simultaneous regression onto a plurality of said data sets. This approach can serve to, for instance, first evaluate system Rotating Compensator Sample System Investigation System Mathematical Model Component Calibration Factors, with a subsequent data acquisition and regression serving to evaluate sample system PSI and DELTA values.

Continuing, as the present invention finds application in Rotating Compensator sample system investigation systems, the following presentation of suitable compensator designs, (depicted in FIGS. 8a–8l), many of which are Claimed in Patents held by the J. A. Woollam Co., is included.

FIGS. 8a–8i demonstrate functional construction of preferred present invention compensator systems.

FIGS. 8j1–8l show additional functional construction of compensator systems which are within the scope of the present invention.

Further, essentially any Compensator which can be placed into a beam of electromagnetic radiation can be applied, such as those disclosed in Claim 9 of U.S. Pat. No. 5,872, 630, (which 630 Patent is incorporated by reference hereinto):

Berek-type;
Non-Berek-type;
Zero Order;
Zero Order comprising a plurality of plates;
Rhomb;
Polymer;
Achromatic Crystal; and
Psuedo-Achromatic.

Figure 8A:
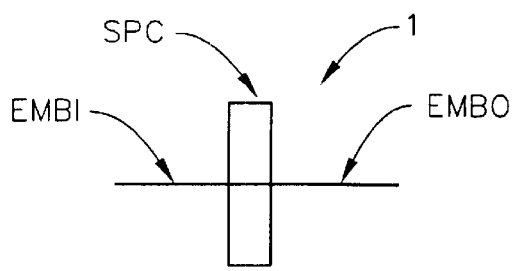
Figure 8B:
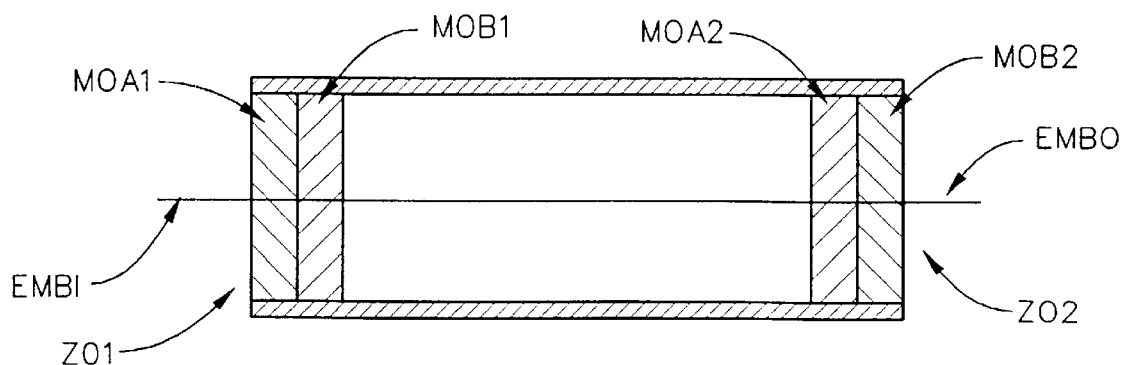
Figure 8C:
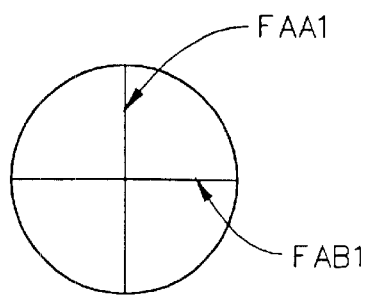
Figure 8D:
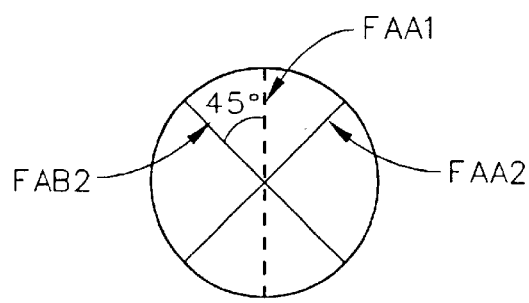

FIGS. 8a, 8b, 8c, 8d and 8e demonstrate functional construction of preferred present invention compensator systems. FIG. 8a simply exemplifies that a single plate (SPC) compensator (1) can be applied. FIG. 8b demonstrates construction of a compensator (2) from first (ZO1) and second (ZO2) effectively Zero-Order, (eg. Quartz or Bicrystaline Cadmium Sulfide or Bicrystaline Cadmium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 8b is a cross-sectional side view of a present invention preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength. FIGS. 8c and 8d are views looking into the left and right ends of the this present invention Compensator (PC) as shown in FIG. 8b, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1).

Figure 8E:
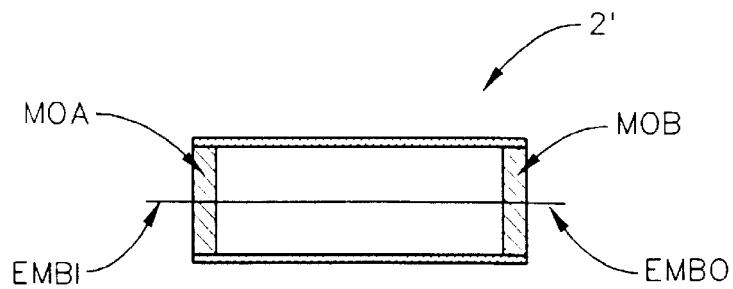

(Note that the fast axis (FAA1) of the first effective Zero-Order Waveplate (ZO1) is shown as a dashed line in FIG. 8d, for reference). FIG. 8e demonstrates functional construction of another preferred compensator (2') which is constructed from two per se. single plate Zero-Order Waveplates (MOA) and (MOB), which are typically made of materials such as mica or polymer.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 8f1–8l demonstrate additional compensators which can be applied in the present invention.

FIG. 8f1 shows that the first additional present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 8f1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational mis-alignments of the input light beam (LB). As well, the total retardence provided is compensated for angular mis-alignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

FIG. 8f2 shows a variation (3') on FIG. 8f1, wherein the first triangular shaped element is replaced by two rotatable reflecting means, identified as (OS1') and (OS2'). This modification allows user adjustment so that the locus of an entering electromagnetic beam (LB') exits undeviated and undisplaced from an entering electromagnetic beam (LB).

Figure 8G:
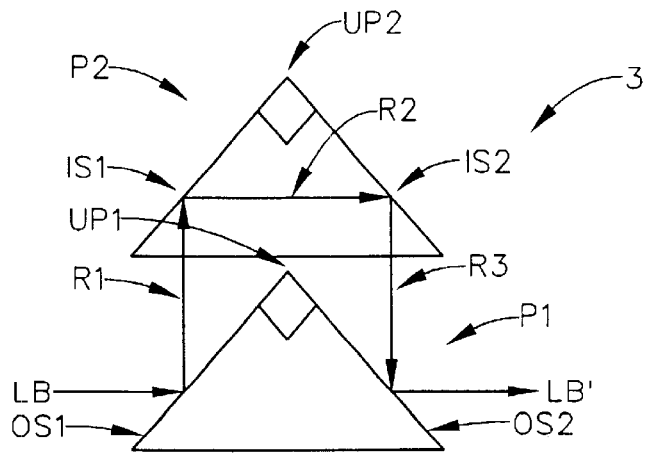
Figure 8G:
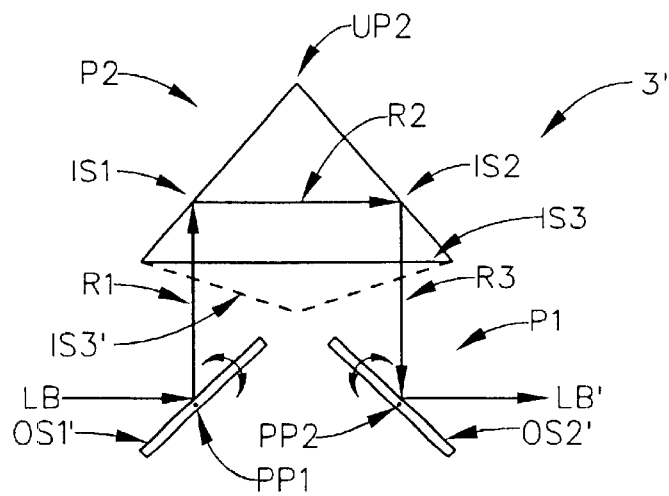
Figure 8G:
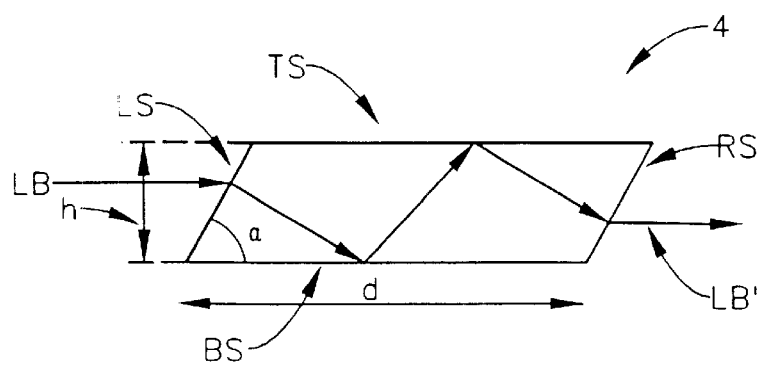

FIG. 8g shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos( )), where alpha ( ) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha ( ) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

$$\frac{d}{h} = 2 - \tan(\phi), \quad \text{where} \quad \phi = \alpha + \sin^{-1}\left(\frac{\sin(90-\alpha)}{n}\right)$$

Figure 8H:
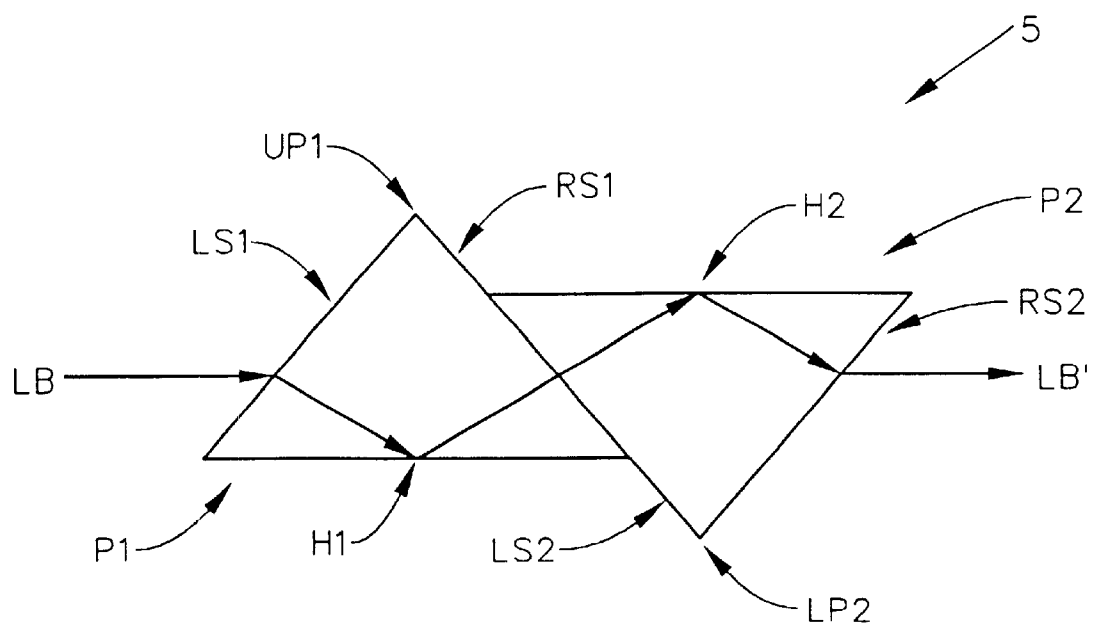

FIG. 8h shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) slides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 8I:
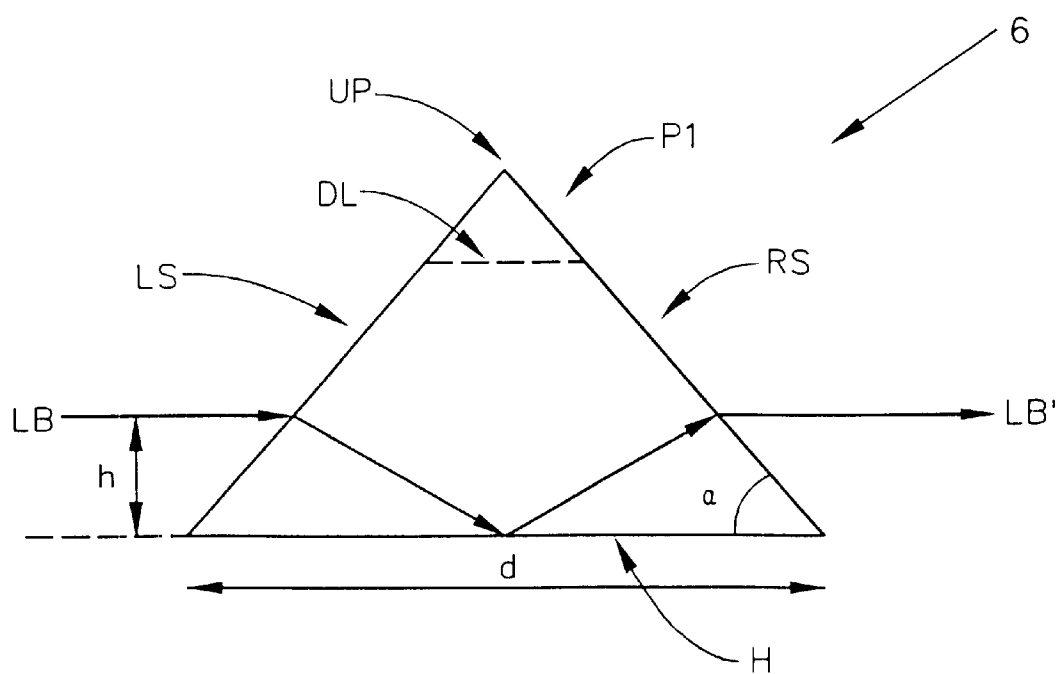

FIG. 8i shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 8i retarder system (6) is typically an isosceles prism which is available off-the-shelf with an angle alpha ( ) of forty-five (45) degrees. As long as the input electromagnetic beam (LB) height (h) is chosen in accordance with the formula:

$$d = 2h\left(\frac{1}{\tan(\alpha)} + \tan(\phi)\right), \quad \text{where} \quad \phi = \alpha + \sin^{-1}\left(\frac{\sin(90-\alpha)}{n}\right)$$

in conjunction with the index of refraction (n) of the material from which the FIG. 6a retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

Figure 8L:
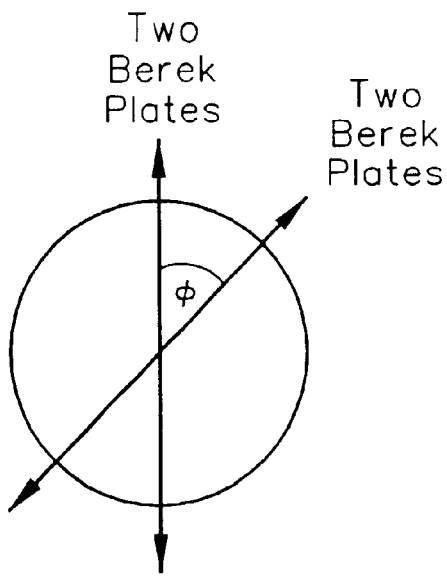
Figure 8L:
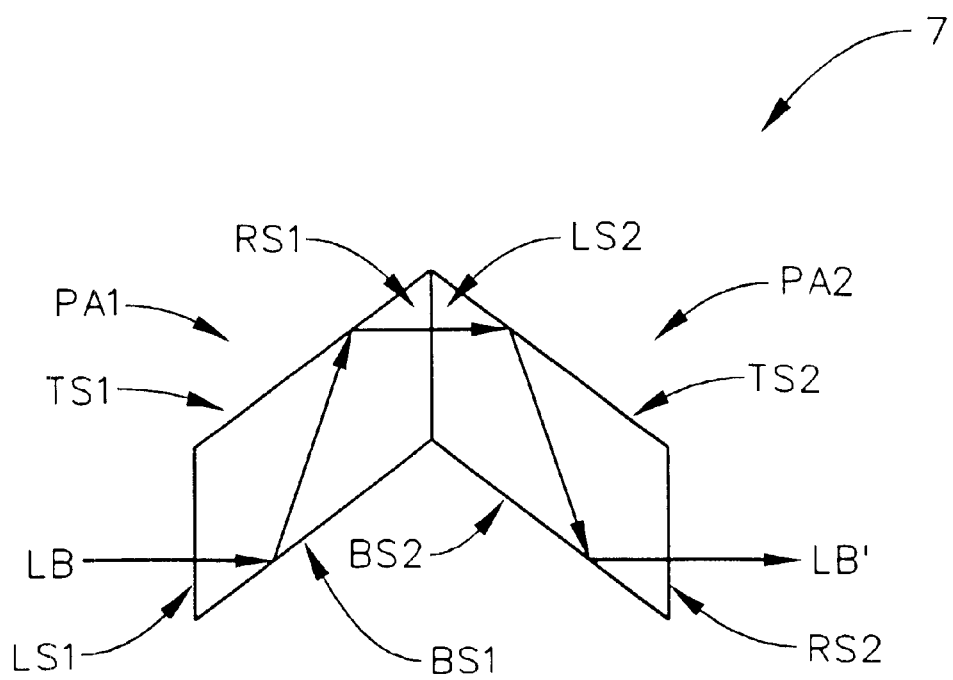

FIG. 8l shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 8j1 shows that the sixth additional present invention retarder system (8) comprises first (BK1) and second (BK2) Berek-type retarders which each have an optical axes essentially perpendicular to a surface thereof. As shown by FIG. 8j2, each of said first (BK1) and second (BK2) Berek-type retarders can have fast axis which are oriented other than parallel to one another, but for the presently described retarder system it is assumed that the fast axes are aligned, (ie. an angle PHI ($\phi$) of zero (0.0) degrees exists between fast axes of the two Berek-type (BK1) and (BK2) plates in FIG. 8j1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately hal of achieved retardence. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 8j2 offset angle PHI ($\phi$) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 8k1 serves as the pictorial reference for the eighth additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 8k2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth present invention retarder system (11) is also pictorially represented by FIG. 8k1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different.

Again, while any compensator can be utilized in the present invention, the foregoing provide insight to suitable designs.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A rotating compensator sample system investigation system comprising a source of a beam of electromagnetic radiation, a polarizer, a stage for supporting a sample system, a beam splitting analyzer means, and at least two detector systems, each said detector system being positioned to separately intercept one of at least two beams which emerges from said beam splitting analyzer means; said rotating compensator sample system investigation system further comprising at least one compensator(s) positioned at a location selected from the group consisting of:

before said stage for supporting a sample system; and after said stage for supporting a sample system; and both before and after said stage for supporting a sample system;

such that when said rotating compensator sample system investigation system is used to investigate a sample system present on said stage for supporting a sample system, said polarizer means and beam splitting analyzer means are maintained essentially fixed in position and at least one of said at least one compensator(s) is caused to continuously rotate while a beam of electromagnetic radiation produced by said source of a beam of electromagnetic radiation is caused to pass through said polarizer means and said at least one compensator(s), said beam of electromagnetic radiation being also caused to interact with said sample system and pass through said beam splitting analyzer means such that two beams of electromagnetic radiation are simultaneously caused to each separately enter different of said at least two detector systems.

2. A rotating compensator sample system investigation system as in claim 1, in which the beam splitting analyzer means is selected from the group consisting of:

Beam Splitting Thompson;

Two Element Wollaston Prism Polarizer;

Three Element Wollaston Prism Polarizer;

Glan-Laser Single Escape Window;

Glan-Laser Double Escape Window; and

Rochon Beam Splitting Prism Polarizer.

3. A rotating compensator sample system investigation system as in claim 1, in which at least one of said at least one compensator(s) is a single element compensator.

4. A rotating compensator sample system investigation system as in claim 1, in which at least one of said at least one compensator(s) is a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees.

5. A rotating compensator sample system investigation system as in claim 1, in which at least one of said at least one compensator(s) is a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1).

6. A rotating compensator sample system investigation system as in claim 1, in which at least one of said at least one compensator(s) is a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1).

7. A rotating compensator sample system investigation system as in claim 1, in which at least one of said at least one compensator(s) is a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB)).

8. A rotating compensator sample system investigation system as in claim 1, in which at least one of said at least one compensator(s) is a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation.

9. A rotating compensator sample system investigation system as in claim 1, in which at least one of said at least one compensator(s) is a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation.

10. A rotating compensator sample system investigation system as in claim 1, in which at least one of said at least one compensator(s) is a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation.

11. A rotating compensator sample system investigation system as in claim 1, in which at least one of said at least one compensator(s) is a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation.

12. A rotating compensator sample system investigation system as in claim 1, in which at least one of said at least one compensator(s) is a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation.

13. A rotating compensator sample system investigation system as in claim 1, in which at least one of said at least one compensator(s) is a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation.

14. A rotating compensator sample system investigation system as in claim 1, in which at least one of said at least one compensator(s) is a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

15. A rotating compensator sample system investigation system as in claim 1, in which at least one of said at least one compensator(s) is a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

16. A method of calibrating a rotating compensator sample system investigation system while extracting sample system PSI and DELTA values, comprising the steps of:

in either order steps a. and b.:
a. providing a rotating compensator sample system investigation system comprising a source of a beam of electromagnetic radiation, a polarizer, a stage for supporting a sample system, a beam splitting analyzer means, and at least two detector systems, each said detector system being positioned to separately intercept one of at least two beams which emerges from said beam splitting analyzer means; said rotating compensator sample system investigation system further comprising at least one compensator(s) positioned at a location selected from the group consisting of:
before said stage for supporting a sample system; and
after said stage for supporting a sample system; and
both before and after said stage for supporting a sample system;
such that when said rotating compensator sample system investigation system is used to investigate a sample system present on said stage for supporting a sample system, said polarizer means and beam splitting analyzer means are maintained essentially fixed in position and at least one of said at least one compensator(s) is caused to continuously rotate while a beam of electromagnetic radiation produced by said source of a beam of electromagnetic radiation is caused to pass through said polarizer means and said at least one compensator(s), said beam of electromagnetic radiation being also caused to interact with said sample system and pass through said beam splitting analyzer means such that at least two beams of electromagnetic radiation are simultaneously caused to each separately enter a different of said at least two detector systems;

b. developing a mathematical model of said rotating compensator sample system investigation system which comprises as calibration parameter variables polarizer azimuthal angle orientation, present sample system PSI, present sample system DELTA, compensator azimuthal angle orientation(s), matrix components of said at least one compensator(s), and at least one effective beam splitting analyzer means azimuthal angle orientation, which mathematical model is effectively a transfer function which enables calculation of electromagnetic beam intensity as a function of wavelength detected by a detector when given intensity as a function of wavelength provided by said source of a beam of electromagnetic radiation;

c. causing a beam of electromagnetic radiation produced by said source of a beam of electromagnetic radiation, to pass through said polarizer, interact with a sample system caused to be in the path thereof, pass through said beam splitting analyzer means such that at least two beams emerge therefrom with each thereof entering a different of said at least two detector systems; said beam of electromagnetic radiation also being caused to pass through said at least one compensator(s) positioned at a location selected from the group consisting of:
before said stage for supporting a sample system;
after said stage for supporting a sample system; and
both before and after said stage for supporting a sample system;

d. simultaneously obtaining two data sets of intensity values of two beams of electromagnetic radiation exiting said beam splitting analyzer means over time, while at least one of said at least one compensator(s) is caused to continuously rotate;

e. performing a mathematical regression of said mathematical model onto said at least two data sets;

said regression based calibration procedure serving to compensate said mathematical model for azimuthal angles of said polarizer, said at least one compensator(s), and said at least one effective analyzer angle(s), in addition evaluating the PSI and DELTA of the present sample system.

17. A method of calibrating a rotating compensator sample system investigation system as in claim 16, which further comprises, in step d. simultaneously obtaining two data sets of intensity values vs. effective azimuthal angles of said beam splitting analyzer means for each of two sample systems; and in step e. including simultaneous regression onto data for both sample systems.

* * * * *